(12) United States Patent
Kwok et al.

(10) Patent No.: US 11,730,909 B2
(45) Date of Patent: Aug. 22, 2023

(54) POSITIVE-AIR-PRESSURE MACHINE CONDUIT

(71) Applicant: ResMed Pty Ltd, Bella Vista (AU)

(72) Inventors: Philip Rodney Kwok, Sydney (AU); Donald Darkin, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 145 days.

(21) Appl. No.: 16/899,712

(22) Filed: Jun. 12, 2020

(65) Prior Publication Data

US 2020/0297959 A1    Sep. 24, 2020

Related U.S. Application Data

(60) Continuation of application No. 16/386,518, filed on Apr. 17, 2019, now Pat. No. 10,744,291, which is a
(Continued)

(30) Foreign Application Priority Data

Apr. 15, 2004   (AU) ............................... 2004902020

(51) Int. Cl.
  *A61M 16/06*  (2006.01)
  *A61M 16/08*  (2006.01)
(52) U.S. Cl.
  CPC .... *A61M 16/0666* (2013.01); *A61M 16/0611* (2014.02); *A61M 16/0683* (2013.01);
(Continued)

(58) Field of Classification Search
  CPC .. A61M 16/0683; A61M 16/08; A61M 16/06; A61M 16/0666; A61M 16/0672;
(Continued)

(56) References Cited

U.S. PATENT DOCUMENTS

| 1,632,449 A | 7/1924 | McKesson |
| 1,710,160 A | 2/1925 | Gibbs |

(Continued)

FOREIGN PATENT DOCUMENTS

| AU | 712236 | 4/1999 |
| AU | 2008906390 | 12/2008 |

(Continued)

OTHER PUBLICATIONS

Notice of Allowance dated Jun. 30, 2020 in parent U.S. Appl. No. 16/386,518.
(Continued)

*Primary Examiner* — Rachel T Sippel
(74) *Attorney, Agent, or Firm* — Nixon & Vanderhye P.C.

(57) ABSTRACT

A conduit for delivering a supply of gas under a positive pressure includes a conduit wall having a first conduit end and a second conduit end. The first conduit end is adapted to be attached to the supply of gas. The conduit wall is deformable between (a) an open condition in which the conduit wall defines a conduit passage along which the supply of gas can travel between the first conduit end to the second conduit end, and (b) a collapsed condition in which the conduit wall substantially collapses the conduit passage.

44 Claims, 7 Drawing Sheets

Related U.S. Application Data continuation of application No. 16/006,209, filed on Jun. 12, 2018, now Pat. No. 11,040,163, which is a division of application No. 15/607,224, filed on May 26, 2017, now Pat. No. 10,029,062, which is a continuation of application No. 11/578,293, filed as application No. PCT/AU2005/000539 on Apr. 15, 2005, now abandoned.

(52) U.S. Cl.
CPC ........ *A61M 16/08* (2013.01); *A61M 16/0833* (2014.02); *A61M 2016/0661* (2013.01); *A61M 2205/0238* (2013.01)

(58) Field of Classification Search
CPC .......... A61M 16/0677; A61M 2016/06; A62B 18/00; A62B 18/02; A62B 18/08; A62B 18/84; A62B 9/00; A62B 7/00; A62B 7/02; A62B 7/12; A62B 7/14
See application file for complete search history.

(56) References Cited

U.S. PATENT DOCUMENTS

| | | |
|---|---|---|
| 1,878,464 A | 9/1932 | Bulmer |
| 2,126,755 A | 8/1938 | Dreyfus |
| 2,130,555 A | 9/1938 | Malcom |
| 2,228,218 A | 1/1941 | Schwartz |
| 2,376,871 A | 5/1945 | Fink |
| 2,578,007 A | 12/1951 | Hill |
| 2,578,621 A | 12/1951 | Yant |
| 2,706,983 A | 4/1955 | Matheson et al. |
| 2,763,263 A | 9/1956 | Ellman |
| 2,931,358 A | 4/1960 | Sherdan |
| 3,172,407 A | 3/1965 | Von Pechmann |
| 3,291,127 A | 12/1966 | Eimer et al. |
| 3,330,273 A | 7/1967 | Bennett |
| 3,388,705 A | 5/1968 | Grosshandler |
| 3,424,633 A | 1/1969 | Corrigall et al. |
| 3,799,164 A | 3/1974 | Rollins |
| 3,802,431 A | 4/1974 | Farr |
| 3,850,171 A | 11/1974 | Ball et al. |
| 3,865,106 A | 2/1975 | Palush |
| 4,052,984 A | 10/1977 | Brockway |
| 4,062,359 A | 12/1977 | Geaghan |
| 4,258,710 A | 3/1981 | Reber |
| 4,266,540 A | 5/1981 | Panzik et al. |
| 4,278,082 A | 7/1981 | Blackmer |
| 4,367,735 A | 1/1983 | Dalli |
| 4,422,456 A | 12/1983 | Tiep |
| 4,437,462 A | 3/1984 | Piljay et al. |
| 4,437,463 A | 3/1984 | Ackerman |
| 4,463,755 A | 8/1984 | Suzuki |
| 4,676,241 A | 6/1987 | Webb et al. |
| 4,774,946 A | 10/1988 | Ackerman |
| 4,782,832 A | 11/1988 | Trimble et al. |
| 4,820,289 A | 4/1989 | Coury et al. |
| 4,878,491 A | 11/1989 | McGilvray, III |
| 4,919,128 A | 4/1990 | Kopala et al. |
| 4,944,310 A | 7/1990 | Sullivan |
| 5,018,519 A | 5/1991 | Brown |
| 5,042,478 A | 8/1991 | Kopala et al. |
| 5,062,421 A | 11/1991 | Burns et al. |
| 5,065,756 A | 11/1991 | Rapoport |
| D322,318 S | 12/1991 | Sullivan |
| 5,117,819 A | 6/1992 | Servidio et al. |
| 5,148,802 A | 9/1992 | Sanders et al. |
| 5,205,832 A | 4/1993 | Tuman |
| 5,243,971 A | 9/1993 | Sullivan et al. |
| 5,269,296 A | 12/1993 | Landis |
| 5,477,852 A | 12/1995 | Landis et al. |
| 5,533,506 A | 7/1996 | Wood |
| 5,538,000 A | 7/1996 | Rudolph |
| 5,560,354 A | 10/1996 | Berthon-Jones et al. |
| 5,644,807 A | 7/1997 | Battistella |
| 5,647,358 A | 7/1997 | Vilasi |
| 5,657,752 A | 8/1997 | Landis et al. |
| 5,662,101 A | 9/1997 | Ogden et al. |
| 5,701,892 A | 12/1997 | Bledstein |
| 5,724,965 A | 3/1998 | Handke et al. |
| 5,746,201 A | 5/1998 | Kidd |
| 5,765,557 A | 6/1998 | Warters |
| 5,782,501 A | 7/1998 | Brandt |
| 5,795,312 A | 8/1998 | Dye |
| 5,921,239 A | 7/1999 | McCall et al. |
| 5,937,851 A | 8/1999 | Serowski et al. |
| 5,989,235 A | 11/1999 | Quacquarella et al. |
| 6,016,804 A | 1/2000 | Gleason et al. |
| 6,112,746 A | 9/2000 | Kwok et al. |
| 6,119,693 A | 9/2000 | Kwok et al. |
| 6,119,694 A | 9/2000 | Correa et al. |
| 6,192,886 B1 | 2/2001 | Rudolph |
| 6,357,440 B1 | 3/2002 | Hansen et al. |
| 6,412,488 B1 | 7/2002 | Barnett et al. |
| 6,431,172 B1 | 8/2002 | Bordewick |
| 6,435,181 B1 | 8/2002 | Jones, Jr. et al. |
| 6,457,473 B1 | 10/2002 | Brostrom et al. |
| 6,467,483 B1 | 10/2002 | Kopacko et al. |
| 6,478,026 B1 | 11/2002 | Wood |
| 6,530,373 B1 | 3/2003 | Patron et al. |
| 6,561,190 B1 | 5/2003 | Kwok et al. |
| 6,561,191 B1 | 5/2003 | Kwok et al. |
| 6,561,193 B1 | 5/2003 | Noble |
| 6,581,594 B1 | 6/2003 | Drew et al. |
| 6,584,976 B2 | 7/2003 | Japuntich et al. |
| 6,615,832 B1 | 9/2003 | Chen |
| 6,631,718 B1 | 10/2003 | Lovell |
| 6,684,882 B1 | 2/2004 | Morine |
| 6,691,707 B1 | 2/2004 | Gunaratnam et al. |
| 6,698,427 B1 | 3/2004 | Clowers |
| 6,796,308 B2 | 9/2004 | Gunaratnam et al. |
| 6,823,865 B2 | 11/2004 | Drew et al. |
| 6,823,869 B2 | 11/2004 | Raje et al. |
| 6,851,425 B2 | 2/2005 | Jaffre et al. |
| 6,863,069 B2 | 3/2005 | Wood |
| 6,892,729 B2 | 5/2005 | Smith et al. |
| 6,907,882 B2 | 6/2005 | Ging et al. |
| 7,007,696 B2 | 3/2006 | Palkon et al. |
| 7,080,645 B2 | 7/2006 | Genger et al. |
| 7,086,422 B2 | 8/2006 | Huber et al. |
| 7,104,491 B2 | 9/2006 | Vinding |
| 7,178,525 B2 | 2/2007 | Matula, Jr. et al. |
| 7,178,526 B2 | 2/2007 | McDonald et al. |
| 7,178,528 B2 | 2/2007 | Lan et al. |
| 7,210,481 B1 | 5/2007 | Lovell et al. |
| 7,219,669 B1 | 5/2007 | Lovell et al. |
| 7,302,950 B2 | 12/2007 | Berthon-Jones et al. |
| 7,318,437 B2 | 1/2008 | Gunaratnam et al. |
| 7,353,827 B2 | 4/2008 | Geist |
| 7,357,136 B2 | 4/2008 | Ho et al. |
| 7,658,189 B2 | 2/2010 | Davidson et al. |
| 7,827,990 B1 | 11/2010 | Melidis et al. |
| 7,856,982 B2 | 12/2010 | Matula, Jr. et al. |
| 7,942,148 B2 | 5/2011 | Davidson et al. |
| 8,443,807 B2 | 5/2013 | McAuley et al. |
| 8,479,741 B2 | 7/2013 | McAuley et al. |
| 8,714,157 B2 | 5/2014 | McAuley et al. |
| 8,944,061 B2 | 2/2015 | D'Souza et al. |
| 8,950,404 B2 | 2/2015 | Formica et al. |
| 8,960,196 B2 | 2/2015 | Hemy |
| 9,027,556 B2 | 5/2015 | Ng et al. |
| 9,119,931 B2 | 9/2015 | D'Souza et al. |
| 9,162,034 B2 | 10/2015 | Veliss et al. |
| 9,242,062 B2 | 1/2016 | Melidis et al. |
| 9,333,315 B2 | 5/2016 | McAuley et al. |
| 9,381,316 B2 | 7/2016 | Ng et al. |
| 9,517,317 B2 | 12/2016 | McAuley et al. |
| 9,539,405 B2 | 1/2017 | McAuley et al. |
| 9,907,922 B2 | 3/2018 | Stephenson et al. |
| 9,907,923 B2 | 3/2018 | Stephenson et al. |
| 9,974,914 B2 | 5/2018 | McAuley et al. |
| 2001/0052778 A1* | 12/2001 | Smith ................ G01R 31/1272 324/541 |

(56) References Cited

U.S. PATENT DOCUMENTS

| | | |
|---|---|---|
| 2002/0005198 A1 | 1/2002 | Kwok et al. |
| 2002/0020416 A1 | 2/2002 | Namey |
| 2002/0029780 A1 | 3/2002 | Frater et al. |
| 2002/0055685 A1 | 5/2002 | Levitsky et al. |
| 2002/0092527 A1 | 7/2002 | Wood |
| 2002/0096173 A1 | 7/2002 | Berthon-Jones et al. |
| 2002/0108613 A1 | 8/2002 | Gunaratnam et al. |
| 2003/0005934 A1 | 1/2003 | Japuntich et al. |
| 2003/0029454 A1 | 2/2003 | Gelinas et al. |
| 2003/0034030 A1 | 2/2003 | Carlucci et al. |
| 2003/0094178 A1 | 5/2003 | McAuley et al. |
| 2003/0121518 A1 | 7/2003 | Ives |
| 2003/0164170 A1 | 9/2003 | Drew et al. |
| 2003/0182710 A1* | 10/2003 | Klotz ............ A41D 13/0025 2/171.3 |
| 2003/0196655 A1 | 10/2003 | Ging et al. |
| 2003/0196658 A1 | 10/2003 | Ging et al. |
| 2003/0200970 A1 | 10/2003 | Stenzler |
| 2004/0003811 A1 | 1/2004 | Bodner |
| 2004/0016432 A1 | 1/2004 | Genger et al. |
| 2004/0025882 A1 | 2/2004 | Madans et al. |
| 2004/0025885 A1 | 2/2004 | Payne |
| 2004/0041342 A1 | 3/2004 | Frieman |
| 2004/0060562 A1 | 4/2004 | McDonald et al. |
| 2004/0065330 A1 | 4/2004 | Landis |
| 2004/0067333 A1 | 4/2004 | Amarasinghe |
| 2004/0103899 A1 | 6/2004 | Noble |
| 2004/0118406 A1 | 6/2004 | Lithgow et al. |
| 2004/0149280 A1 | 8/2004 | Semeniuk |
| 2004/0182398 A1 | 9/2004 | Sprinkle et al. |
| 2004/0186405 A1 | 9/2004 | Pinna et al. |
| 2004/0211428 A1 | 10/2004 | Jones, Jr. et al. |
| 2004/0226566 A1 | 11/2004 | Gunaratnam et al. |
| 2004/0234610 A1 | 11/2004 | Hall et al. |
| 2004/0255949 A1 | 12/2004 | Lang et al. |
| 2005/0001152 A1 | 1/2005 | Stewart et al. |
| 2005/0011524 A1 | 1/2005 | Thomlinson et al. |
| 2005/0025816 A1 | 2/2005 | Tanaka |
| 2005/0028822 A1 | 2/2005 | Sleeper et al. |
| 2005/0061326 A1 | 3/2005 | Payne, Jr. |
| 2005/0066976 A1 | 3/2005 | Wondka |
| 2005/0092326 A1 | 5/2005 | Drew et al. |
| 2005/0092329 A1 | 5/2005 | Sta-Maria |
| 2005/0121030 A1 | 6/2005 | Bateman et al. |
| 2005/0126574 A1 | 6/2005 | Wood |
| 2005/0155604 A1 | 7/2005 | Ging et al. |
| 2005/0199242 A1 | 9/2005 | Matula |
| 2005/0205096 A1 | 9/2005 | Matula, Jr. et al. |
| 2005/0241644 A1 | 11/2005 | Gunaratnam |
| 2006/0011198 A1* | 1/2006 | Matarasso ........ A61M 16/127 128/204.18 |
| 2006/0042629 A1 | 3/2006 | Geist |
| 2006/0060200 A1 | 3/2006 | Ho et al. |
| 2006/0112962 A1 | 6/2006 | Tebbutt et al. |
| 2006/0118117 A1 | 6/2006 | Berthon-Jones et al. |
| 2006/0124131 A1 | 6/2006 | Chandran et al. |
| 2006/0174889 A1 | 8/2006 | Noble |
| 2006/0180151 A1 | 8/2006 | Rinaldi |
| 2006/0201514 A1 | 9/2006 | Jones et al. |
| 2006/0272646 A1 | 12/2006 | Ho et al. |
| 2007/0044804 A1 | 3/2007 | Matula, Jr. et al. |
| 2007/0045152 A1 | 3/2007 | Kwok et al. |
| 2007/0074723 A1 | 4/2007 | Coury et al. |
| 2007/0175480 A1 | 8/2007 | Gradon et al. |
| 2007/0246043 A1 | 10/2007 | Kwok et al. |
| 2008/0000477 A1 | 1/2008 | Huster et al. |
| 2008/0006277 A1 | 1/2008 | Worboys et al. |
| 2008/0110464 A1 | 5/2008 | Davidson et al. |
| 2009/0044808 A1 | 2/2009 | Guney et al. |
| 2010/0236552 A1 | 9/2010 | Kwok et al. |
| 2011/0072553 A1 | 3/2011 | Ho |
| 2014/0083430 A1 | 3/2014 | Matula, Jr. et al. |
| 2017/0266404 A1 | 9/2017 | Kwok et al. |
| 2018/0289914 A1 | 10/2018 | Kwok et al. |
| 2019/0184124 A1 | 6/2019 | Kwok et al. |
| 2019/0184125 A1 | 6/2019 | Kwok et al. |
| 2019/0192801 A1 | 6/2019 | Kwok et al. |
| 2019/0192802 A1 | 6/2019 | Kwok et al. |
| 2019/0240439 A1 | 8/2019 | Kwok et al. |

FOREIGN PATENT DOCUMENTS

| | | |
|---|---|---|
| AU | 2009900327 | 1/2009 |
| AU | 2009902731 | 6/2009 |
| AU | 2009904236 | 9/2009 |
| DE | 100 51 891 | 5/2002 |
| DE | 101 05 383 | 8/2002 |
| EP | 0 697 225 A2 | 2/1996 |
| EP | 1 027 905 | 8/2000 |
| EP | 1 147 782 | 10/2001 |
| EP | 1 149 603 A2 | 10/2001 |
| EP | 1 314 445 A | 5/2003 |
| EP | 1 396 277 A2 | 10/2004 |
| JP | 2000-507887 | 6/2000 |
| WO | WO 1998/024499 | 6/1998 |
| WO | WO 1998/024499 | 11/1998 |
| WO | WO 00/50122 A1 | 8/2000 |
| WO | WO 2000/076568 | 12/2000 |
| WO | WO 2001/032250 | 5/2001 |
| WO | WO 2001/062326 | 8/2001 |
| WO | WO 02/47749 A1 | 6/2002 |
| WO | WO 2004/022147 A1 | 3/2004 |
| WO | WO 2004/041341 A1 | 5/2004 |
| WO | WO 2004/041342 A1 | 5/2004 |
| WO | WO 2004/073778 A1 | 9/2004 |
| WO | WO 2005/018523 A2 | 3/2005 |
| WO | WO 2005/021075 A1 | 3/2005 |
| WO | WO 2005/051468 A1 | 6/2005 |
| WO | WO 2005/076874 A3 | 8/2005 |
| WO | WO 2005/079726 A1 | 9/2005 |
| WO | WO 2005/086943 A2 | 9/2005 |
| WO | WO 2005/099801 A1 | 10/2005 |
| WO | WO 2005/123166 A1 | 12/2005 |
| WO | WO 2006/000046 A1 | 1/2006 |
| WO | WO 2006/074515 A1 | 7/2006 |
| WO | WO 2006/130903 A1 | 12/2006 |
| WO | WO 2007/006089 A1 | 1/2007 |
| WO | WO 2007/014088 A2 | 2/2007 |
| WO | WO 2007/045008 A1 | 4/2007 |
| WO | WO 2007/048174 A1 | 5/2007 |
| WO | WO 2007/147088 A2 | 12/2007 |
| WO | WO 2008/007985 A1 | 1/2008 |
| WO | WO 2008/011682 A1 | 1/2008 |
| WO | WO 2008/011683 A1 | 1/2008 |
| WO | WO 2008/030831 A2 | 3/2008 |
| WO | WO 2008/068966 A1 | 6/2008 |
| WO | WO 2009/026627 A1 | 3/2009 |
| WO | WO 2009/052560 A1 | 4/2009 |
| WO | WO 2009/059353 A1 | 5/2009 |
| WO | WO 2010/066004 A1 | 6/2010 |

OTHER PUBLICATIONS

ACP Composites—Large Stock of Ready to Use Composite Plate, Tube, Sheet, Fabrics and Core Materials, https://www.acpsakes.com/Core-Materials-nd-Foam.html, dated Oct. 5, 2015, 4 pages.

Flexifit instructions, http://web.archive.org/web/1 9970126045828/ http:/www.archive.org/ dated Jan. 26, 1997, Affidavit of Christopher Butler dated Sep. 6, 2016, 23 pages.

Guidelines for Sandwich Core Materials, http://fibreglast.com/product/guidelines-for-sandwich-core-materials/Learning_Center, dated Oct. 5, 2015, 3 pages.

http://pdf.medicalexpo.com [online], "Opus Brochure," Fisher & Paykel Healthcare, available on or before Apr. 25, 2015, via Internet Archive: Wayback Machine URL <https://web.archive.org/web/20150425003833/http://pdf.medicalexpo.com/pdf/fisher-paykel-healthcare/opus-specification-sheet/70844-126507.html> [retrieved on Apr. 30, 2019], retrieved from: URL <www.fphcare.com>, 18 pages.

Malloy, Plastic Part Design for Injection Molding, New York: Hanser Publishers, 1994, 14 pages.

(56) References Cited

OTHER PUBLICATIONS

ResMed Mask Frames, Nasal Cushions and Headgear, http://web.archive.org/web/19970126045828/http://www.archive.org/ dated Jan. 26, 1997, Affidavit of Christopher Butler dated Jul. 6, 2017, 8 pages.
ResMed Mirage Swift Nasal Pillows System, www.resmed.com, 2004, 6 pages.
ResMed Mirage Vista Nasal Mask-Component Cards, www.resmed.com Reference No. 1010279/30502, dated 2005, 1 page.
ResMed Origins Brochure dated Apr. 17, 2016, 64 pages.
Ultra Mirage Full Face Mask brochure, http://web.archive.org/web/19970 1 26045828/http://www.archive.org/ dated Jan. 26, 1997, Affidavit of Christopher Butler dated Sep. 6, 2016, 9 pages.
Users Guide ResMed Mirage Swift Nasal Pillows System, www.myresmed.com dated May 6, 2004, 11 pages.
Kwok et al, U.S. Appl. No. 16/280,625, filed Feb. 20, 2019 for "Positive-Air-Pressure Machine Conduit," downloaded May 14, 2020, 2394 pages.
Kwok et al, U.S. Appl. No. 16/283,218, filed Feb. 22, 2019 for "Positive-Air-Pressure Machine Conduit," downloaded May 18, 2020, 2364 pages.
Kwok et al., U.S. Appl. No. 16/287,040, filed Feb. 27, 2019 for "Positive-Air-Pressure Machine Conduit," downloaded May 14, 2020, 2366 pages.
Kwok et al, U.S. Appl. No. 16/290,377, filed Mar. 1, 2019 for "Positive-Air-Pressure Machine Conduit," downloaded May 14, 2020, 2370 pages.
International Preliminary Report on Patentability, International Application No. PCT/AU2005/000539, (dated Oct. 19, 2006), 6 pgs.
Supplementary Search Report issued in EP 05 72 9680 dated Sep. 18, 2009.
Office Action issued in CN 200580011118.3 dated Nov. 27, 2009.
Examination Report issued in NZ 550423 dated Mar. 13, 2009.
Instruction Brochure for "E-vent-N" Aug. 1997, ©Dräger Medizintechnik GmbH, 2 pages.
European Search Report for PCT/EP2004/007599, dated Dec. 17, 2004, 10 pages.
U.S. Appl. No. 10/563,857, filed Jan. 9, 2006, Madaus et al.
U.S. Appl. No. 60/640,184, filed Dec. 2004, Henry et al.
Examination Report for Co-Pending NZ Application No. 583929, dated Mar. 22, 2010, 3 pages.
Office Action for co-pending JP Application No. 2007-507626, dated Sep. 7, 2010, 4 pages, with English translation.
Examination Report for corresponding NZ Appln No. 583929, dated Sep. 20, 2011, 2 pages.
Decision of Rejection and English Translation for corresponding JP Appln. No. 2007-507626, dated Sep. 20, 2011, 4 pages.
Office Action issued in related CN Appln. No. 200580011118.3 (dated Feb. 22, 2012).
Office Action issued in a corresponding Japanese Application No. 2011-047484 (dated Aug. 7, 2012) with English translation thereof.
Further Examination Report dated Dec. 18, 2012 issued in corresponding New Zealand Application No. 595133.
Office Action issued in a corresponding Japanese Application No. 2012-009839 (dated Feb. 5, 2013) with English translation thereof.
First Examination Report issued in corresponding Indian Patent Application No. 6006/DELNP/2006 dated Feb. 2, 2013.
Decision of Rejection (with English-language translation) issued in a corresponding Japanese Patent Application No. 2011-047484 dated Jul. 2, 2013.
Non-final Office Action issued in related U.S. Appl. No. 10/563,857 dated Oct. 7, 2013.
U.S. Appl. No. 11/645,582, filed Dec. 2006, Kwok et al.
U.S. Appl. No. 11/417,234, filed May 2006, Huber et al.
U.S. Appl. No. 10/364,358 filed Feb. 2003, Kwok et al.
U.S. Appl. No. 10/298,845 filed Nov. 2002, Kwok et al.
Decision of Rejection issued in a corresponding Japanese Application No. 2012-009839 on Dec. 24, 2013 with English-language translation.
International Search Report for PCT/AU2005/000539 dated Jun. 21, 2005.
Appeal Decision dated Jul. 7, 2014 in corresponding Japanese Patent Application No. 2011-47484 with English translation thereof.
Examiner's Answer dated Jun. 3, 2015, in a related U.S. Appl. No. 10/563,587 (27 pages).
Office Action for co-Pending EP Application No. 05729680.8, dated Jul. 19, 2010 (6 pages).
Examiner Report for Co-Pending AU Application No. 2005232337, dated Mar. 31, 2010 (2 pages).
Notice of Allowance dated Dec. 22, 2020 in corresponding U.S. Appl. No. 16/290,377 (11 pages).
Office Action dated Jun. 3, 2021 in corresponding U.S. Appl. No. 17/178,388 (45 pages).
Office Action dated Aug. 11, 2021 in corresponding U.S. Appl. No. 17/243,681 (39 pages).
Final Office Action dated Oct. 8, 2021 in corresponding U.S. Appl. No. 17/178,388, citing WO 2012/123891 (Haibach), (11 pages).

\* cited by examiner

POSITIVE-AIR-PRESSURE MACHINE CONDUIT

CROSS-REFERENCE TO APPLICATIONS

This application is a continuation of U.S. application Ser. No. 16/386,518, filed Apr. 17, 2019, which is a continuation of U.S. application Ser. No. 16/006,209, filed Jun. 12, 2018, which is a divisional application of U.S. application Ser. No. 15/607,224, filed May 26, 2017, now U.S. Pat. No. 10,029,062, which is a continuation of U.S. application Ser. No. 11/578,293, filed Oct. 13, 2006, now abandoned, which is the US national phase of international application PCT/AU2005/000539 filed Apr. 15, 2005, which designated the U.S. and claimed the benefit of AU 2004902020 filed Apr. 15, 2004, the entire contents of each of which are hereby incorporated herein by reference.

FIELD OF THE INVENTION

The present invention relates to a positive-air-pressure (PAP) machine conduit. The present invention also relates to headgear including such a conduit and to nose pieces including such a conduit.

BACKGROUND OF THE INVENTION

One of the main factors influencing the success or failure of a patient to adopt a CPAP apparatus used in the treatment of obstructive sleep apnea is the patient's ability to handle the discomfort of the headgear and supply conduit associated with such apparatus.

Such apparatus can tend to limit a patient's ability to move or roll during sleep, thus adding to the potential discomfort for a patient.

Therefore, a need has developed in the art to overcome or ameliorate at least some of the disadvantages of such apparatus, or to provide a useful alternative.

SUMMARY OF THE INVENTION

One aspect of the invention relates to a conduit for delivering a supply of gas under a positive pressure. The conduit includes a conduit wall having a first conduit end and a second conduit end. The first conduit end is adapted to be attached to the supply of gas. The conduit wall is deformable between (a) an open condition in which the conduit wall defines a conduit passage along which the supply of gas can travel between the first conduit end to the second conduit end, and (b) a collapsed condition in which the conduit wall substantially collapses the conduit passage.

Another aspect of the invention relates to headgear for delivering a supply of gas under a positive pressure to a patient. The headgear includes a connector adapted to be attached to the supply of gas. A pair of side portions are adapted to extend along opposite sides of the patient's head. Each of the side portions defines a conduit having a first conduit end attached to the connector and a second conduit end adapted to be positioned adjacent the patient's nose. A head attachment structure is adapted to releasably secure the headgear to the patient's head.

Another aspect of the invention relates to a nasal assembly for delivering a supply of gas under a positive pressure to a patient. The nasal assembly includes a connector adapted to be attached to the supply of gas, a nose-piece adapted to engage the patient's nose, and a pair of side portions adapted to extend along opposite sides of the patient's head. Each of the side portions defines a conduit having a first conduit end attached to the connector and a second conduit end adapted to connect to the nose-piece. A head attachment structure is adapted to releasably secure the headgear to the patient's head.

Another aspect of the invention relates to a method for using a conduit to deliver a supply of gas under a positive pressure. The method includes providing a conduit including a conduit wall having a first conduit end and a second conduit end. The conduit wall is deformable between (a) an open condition in which the conduit wall defines a conduit passage along which the supply of gas can travel between the first conduit end to the second conduit end, and (b) a collapsed condition in which the conduit wall substantially collapses the conduit passage. The method includes connecting the first conduit end of the conduit to the supply of gas, delivering the supply of gas into the conduit via the first conduit end such that the supply of gas urges the conduit wall into the open condition to allow the supply of gas to travel from the first conduit end to the second conduit end, and disposing the second conduit end of the conduit at a position at which the supply of gas is to be delivered.

Another aspect of the invention relates to a method for constructing headgear that delivers a supply of gas under a positive pressure to a patient. The method includes providing headgear including at least one conduit that defines a conduit passage along which the supply of gas can travel, mapping the shape of a particular patient's head, and forming the headgear into a headgear shape in accordance with the mapping such that the headgear achieves a substantially close and comfortable fit on the particular patient's head.

Another aspect of the invention relates to a positive-air-pressure (PAP) machine conduit. The conduit includes flexible conduit walls, a first conduit end adapted for attachment to a supply of gas under a positive pressure, and a second conduit end. The conduit is configured such that when the first end is connected to the supply, the gas urges the conduit walls into a first condition in which the walls define a conduit passage along which the gas travels from the first end to the second end. The conduit is deformable into a second condition in which the passage is substantially collapsed.

In an embodiment, the conduit may be formed from a single piece of sheet material.

In another embodiment, the conduit may be formed from at least two pieces of sheet material which are joined together.

In another embodiment, the conduit may be formed from woven sheet material. In yet another embodiment, the conduit may be formed from flexible polymeric sheet material, which in an embodiment may be an elastic material.

In another embodiment, the material may a lamination of a plurality of materials. In forms of this embodiment, the material may be a lamination of a thin foam layer and a fabric layer which, in one form, is coated on the foam layer, or felt flocking which, in one form, is coated on the foam layer. Such embodiments may provide a soft, warm comfortable feel against the skin of a patient using the conduit.

In another embodiment, parts of the conduit which are adapted to be in contact with the skin of a patient may be of gel-like material.

In yet another embodiment, the conduit walls may be configured to permit the leaking of gas therethrough from the passage.

In yet another embodiment, the conduit walls may include wall portions in the form of double walls defining a substantially gas tight space between them.

In still another embodiment, the conduit walls may be substantially devoid of elasticity. In another embodiment, the conduit walls may have elasticity so as to be expandable. In yet further embodiments, the conduit walls may have at least one region with elasticity and at least one other region substantially devoid of elasticity, and/or different regions of differing amounts of elasticity.

Another aspect of the invention relates to a positive-air-pressure (PAP) headgear. The headgear includes connection means for connection in fluid-flow communication to a supply of gas configured for providing gas under a positive pressure and a pair of conduits according to above-noted aspects of the invention or embodiments thereof. The conduits are configured to extend around opposite sides of a patient's head. The first end of each conduit is connected in fluid-flow communication to the connection means and the second end of each conduit is configured, when the headgear is being worn by the patient, to be positioned adjacent the patient's nose. Head attachment means releasably secures the headgear to the patient's head.

In an embodiment, the second end may be configured to be connected to a nose-piece for directing gas that has passed along the passages from the second ends to within the patient's nose.

In another embodiment, the headgear may be configured, when the headgear is being worn by the patient, for the conduits to extend across the patient's nose. The headgear may define a pair of apertures opening into the conduits and positioned to be adjacent the patient's nose for attachment of at least one nose-piece for directing gas that has passed along the passages to within the patient's nose.

In this case, in one embodiment, the second ends may be integrally joined to each other.

Also in this case, the headgear may be provided with a pair of seal rings, each joined to the headgear at a respective aperture for establishing a close seal with the at least one nose-piece.

In another embodiment, the material from which each conduit is formed may be adapted to permit the passage of water vapour therethrough to enhance patient comfort particularly in a warm climate, but is substantially air tight.

In another embodiment, the head attachment means may include a strap joined to at least one of the pair of conduits.

In another embodiment, the pair of conduits and at least part of the connection means may be integral with one another in a unitary construction.

In another embodiment, the pair of conduits, at least part of the connection means, and the strap are integral with one another in a unitary construction.

In yet another embodiment, the headgear may be configured such that the strap extends around a portion of the head posterior to the apex.

In yet another embodiment, the headgear may be configured such that, when the headgear is being worn by the patient, the connection means may be disposed at a position adjacent to or anterior of the apex of the patient's head.

In an embodiment, the headgear may be configured such that, when the connection means is connected in fluid-flow communication to a supply of gas with the supply of gas providing gas under a positive pressure so that the gas travels along the pair of conduits, collapsing of the passage of one of the conduits due to compression being applied to that conduit, which collapsing results in a decrease in the volume flow rate of gas through that passage, results in a deformation of the passage of the other conduit and an associated increase in volume flow rate of gas through the passage of that other conduit.

The headgear may be configured such that, as a result of the deformation of the passage of the other conduit, the total volume flow rate of the gas through the pair of conduits remains substantially constant during the collapsing of the passage of the one conduit.

In an embodiment, the collapsing of the passage of the one conduit is deformation which causes a change in the ratio between a height extent and a lateral extent of that passage. In one embodiment, the height extent decreases and the lateral extent increases. Similarly, in another embodiment, the deformation of the passage of the other conduit is deformation which causes a change in the ratio between a height extent and a lateral extent of that passage. In one embodiment, the height extent increases and the lateral extent decreases.

In another embodiment, the headgear may include an adjustable head cap with the conduits being attached to the cap at opposite sides thereof. In this case, the cap may constitute the attachment means, and the connection means may be mounted on the cap.

In yet another embodiment, the conduits may be detachable from the attachment means so that the attachment means may be selectively releasably connected with differently sized and/or shaped conduits. In this case, the conduits may be selectively releasably connected with differently sized and/or shaped attachment means, whereby the headgear may form part of a modular headgear system having interchangeable attachment means and conduits.

In an embodiment, the headgear may be adapted for use with a patient mask configured to fit the patient's head adjacent the patient's nose to direct gas from the conduits to the nose. Then, the headgear may be adapted to be detachable from the mask to enable the patient to selectively remove the mask from the headgear and hence from the patient's head while the headgear continues to be being worn by the patient.

Yet another aspect of the invention relates to a nose-piece configured for attachment to a headgear, according to above-noted aspects of the invention or embodiments thereof, for directing air from the second end of a conduit to the interior of the patient's nose.

In an embodiment, the nose-piece may include a conduit according to above-noted aspects of the invention or embodiments thereof.

In another embodiment, the flexible conduit walls may be double walls defining a substantially gas-tight space between them.

In another embodiment, the nose-piece may include a nozzle opening into the space to enable the delivery of gas into the space to inflate the nose-piece.

In another embodiment, the nose-piece may be a conduit according to above-noted aspects of the invention or embodiments thereof.

In another embodiment, the nose-piece may include a pair of nostril formations for being received in a patient's nose and for directing gas from the conduit passage into the nose. Then, in an embodiment, the conduit may define a pair of nostril formation apertures, each nostril formation extending through a respective nostril formation aperture.

In another embodiment, the nostril formations may be customized to closely fit the nostrils of a particular patient.

In yet another embodiment, parts of the headgear which are adapted to be in contact with the skin of a patient may be of gel-like material.

Still another aspect of the invention relates to a method of using a PAP machine conduit, according to above-noted aspects of the invention or embodiments thereof, for delivering air. The method includes connecting the first end of the conduit to a supply means configured for supplying air under a positive pressure, delivering air by the machine to the conduit via the first end such that the air urges the conduit walls into the first condition, and disposing the second end at a position at which the air is to be delivered such that the air that has passed along the passage exits the conduit at the second end.

Still another aspect of the invention relates to a method of providing a PAP headgear for use by a particular patient. The headgear includes connection means for connection in fluid-flow communication to a supply of gas configured for providing gas under a positive pressure, a pair of conduits configured to extend around opposite sides of the particular patient's head, and head attachment means to releasably secure the headgear to the particular patient's head. Each conduit has flexible conduit walls, a first conduit end connected in fluid-flow communication to the connection means, and a second conduit end configured, when the headgear is being worn by the particular patient, to be positioned adjacent the particular patient's nose. Each conduit is configured such that when the connection means is connected to the supply, the gas urges the conduit walls into a first condition in which the walls define a respective conduit passage along which the gas travels from the respective first end to the respective second end and wherein each conduit is compressibly deformable into a second condition in which the passage is substantially collapsed. The method includes mapping the shape of the particular patient's head, and forming the headgear into a headgear shape in accordance with the mapping such that the headgear, when fitted to the particular patient's head, is a close fit thereon.

In an embodiment, the method may include after mapping the shape of the particular patient's head, forming a head template in accordance with the mapping. Also, the forming the headgear into a headgear shape may include forming the headgear in accordance with the shape of the template.

In another embodiment, the mapping the shape of the particular patient's head may be carried out manually, while in another embodiment, the mapping the shape of the particular patient's head may be carried out by mapping means which are at least partially automated.

When the mapping the shape of the particular patient's head is carried out by mapping means which are at least partially automated, the mapping means may include a computer.

When the mapping the shape of the particular patient's head is carried out by mapping means which are at least partially automated, the mapping the shape of the patient's head may include touchless sensing of the shape of the patient's head. The touchless sensing may involve the use of a camera or a laser sensor.

In an embodiment, the headgear may be a type of headgear having at least two pieces of sheet material which are joined together, wherein the forming the headgear into a headgear shape in accordance with the mapping includes forming each of the pieces into a respective sheet shape configured to enable the achievement of the headgear shape when the headgear is formed, and joining the pieces of sheet material together in the forming of the headgear.

In another embodiment, the joining the pieces of sheet material together in the forming of the headgear includes joining the pieces of sheet material along predetermined joint paths to define detachment areas adjacent the joint paths in which the pieces of sheet material are detached from each other.

The joint paths may constitute lines of fold lines to facilitate curving of the joined pieces of sheet material in the forming of the headgear into the headgear shape.

Each joint path may be of a zig-zag configuration, and may be substantially sinusoidal so as to define peaks and troughs.

In this case, adjacent pairs of the joint paths may be positioned relative to each other so that each peak of one joint path of the pair is aligned with a respective trough of the other joint path and vice versa, whereby the detachment areas may be substantially diamond-shaped.

Other aspects, features, and advantages of this invention will become apparent from the following detailed description when taken in conjunction with the accompanying drawings, which are a part of this disclosure and which illustrate, by way of example, principles of the invention.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

Figure 1:
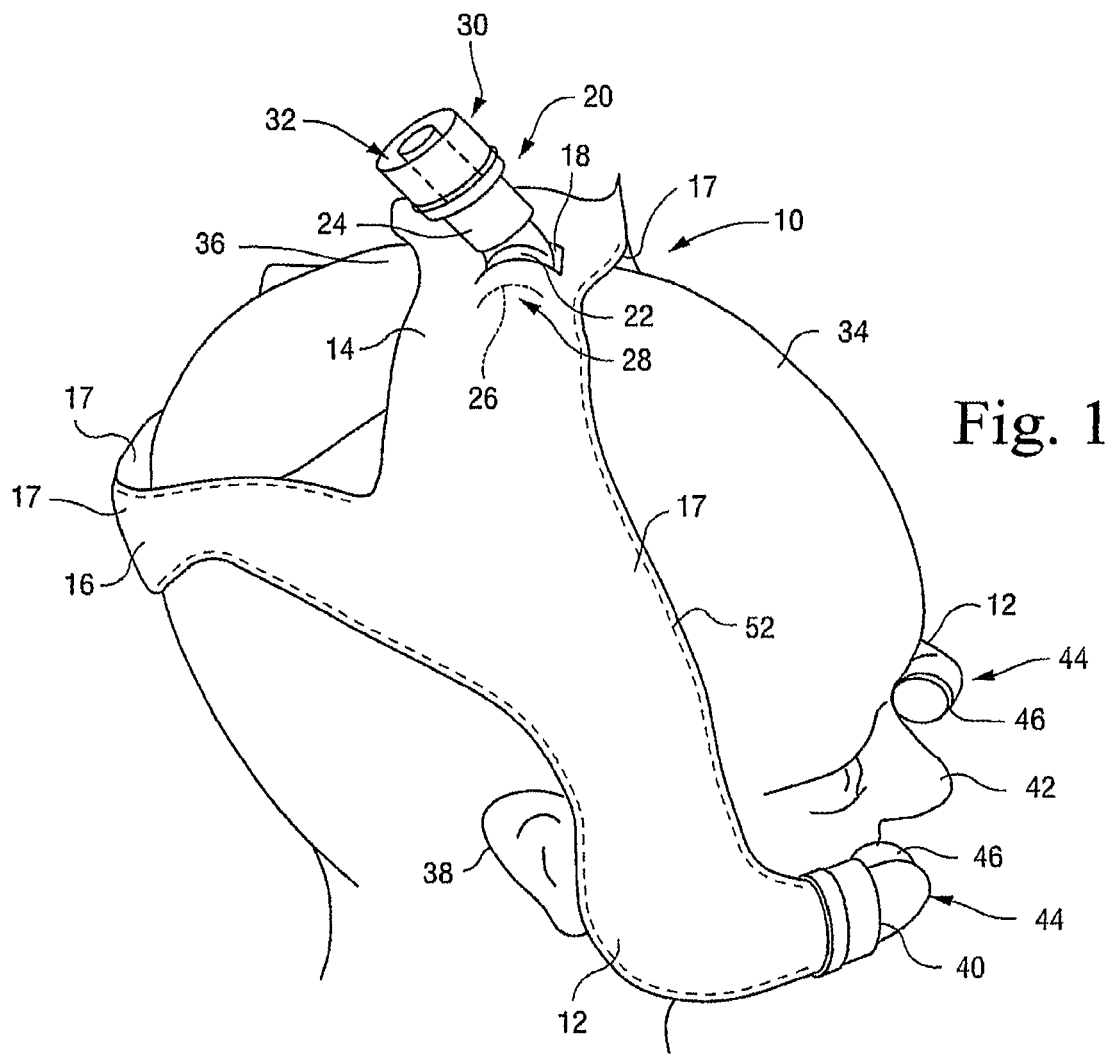
FIG. 1 is a perspective view of a headgear according to an embodiment of the invention, the headgear in a position of use.
Figure 2:
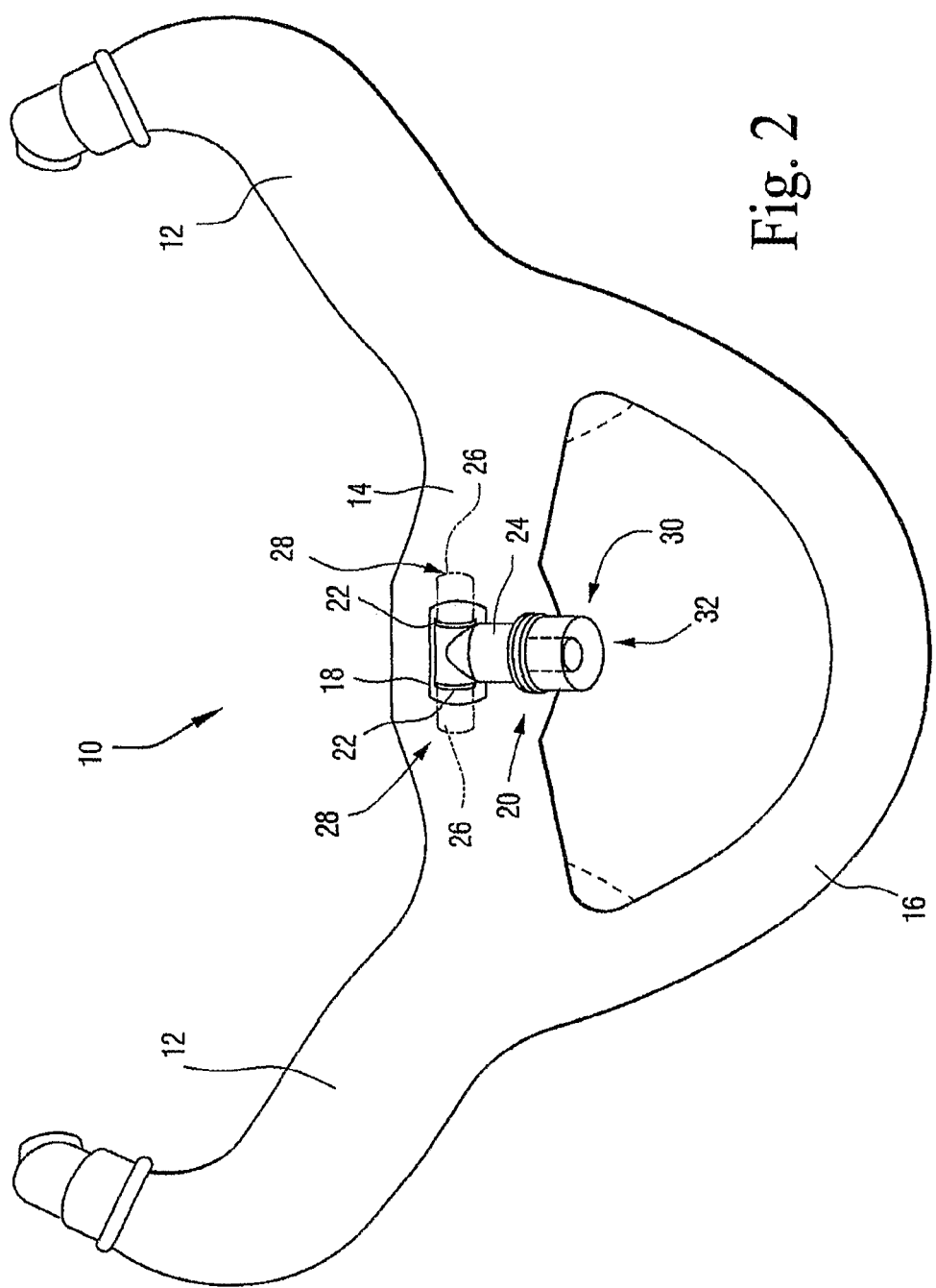
FIG. 2 is a plan view of the headgear of FIG. 1 shown in a flattened-out condition (i.e., not in a position of use)

Referring to FIGS. 1 and 2, there is shown a patient interface including a headgear 10 according to an embodiment of the invention. The headgear 10 includes a pair of conduits or side portions 12 which are joined integrally to each other by a central portion 14 via joints. A head attachment means in the form of a strap 16 is also joined integrally to the side portions 12 as shown in FIG. 1, so that the side portions 12, central portion 14, and strap 16 are all of an integral, unitary construction.

The side portions 12, central portion 14 and strap 16 are formed by joining together, e.g., by high-frequency (HF) plastics welding, a pair of polymeric (e.g., plastic) sheets 17. The manner in which the sheets 17 are joined together is such that the middle portions of the sheets 17 can be parted from each other to define passages running along the length of the side portions 12, as described in more detail below. It will be appreciated that, when the sheets 17 are configured to form such passages in the side portions 12, the side portions 12 constitute conduits, and will be referred to as such below. The sheets 17 may be joined together in any suitable manner to form such passages in the side portions 12.

The conduits 12, at the positions where the sheets 17 are joined together (e.g., by plastics welding), may be provided with inwardly extending pleats (e.g., V-shaped recesses extending inwardly with respect to the conduits) to facilitate the parting of the middle portions of the sheets 17 and hence the formation of the passages, as referred to above.

The central portion 14 has an aperture 18 at the center thereof. The headgear 10 includes a T-connection or T-shaped connector 20 which extends into the aperture 18. The T-connection 20 includes a pair of side pipes 22 and a central pipe 24 which opens into the side pipes 22. The side pipes 22 extend, in opposite directions, between the plastic sheets 17, with the center pipe 24 protruding from the central portion 14 via the aperture 18. The side pipes 22 are firmly engaged with the plastic sheets 17 so as to form a substantially air-tight seal with the sheets 17, while permitting some rotational movement along the joints between the side pipes 22 and the sheets 17.

The positions of the ends 26 of the side pipes 22 (indicated in broken lines in FIGS. 1 and 2) also serve to mark the transition from the central portion 14 to the respective side portions 12. Accordingly, the positions of the conduits 12 corresponding to the ends 26 of the side pipes 22 constitute first upper ends 28 of the conduits 12.

An attachment formation or swivel 30 which has a cylindrical union 32 at its end, is mounted around the center pipe 24 so as to be rotatable relative to the center pipe 24. As discussed further below, the attachment formation 30 is for receiving the end (not shown) of an air supply pipe leading from a flow generator or an air supply means (also not shown) for supplying air under pressure to the headgear 10, so as to connect the air supply pipe in fluid-flow communication with the center pipe 24 while permitting rotation of the air supply pipe.

Figure 3:
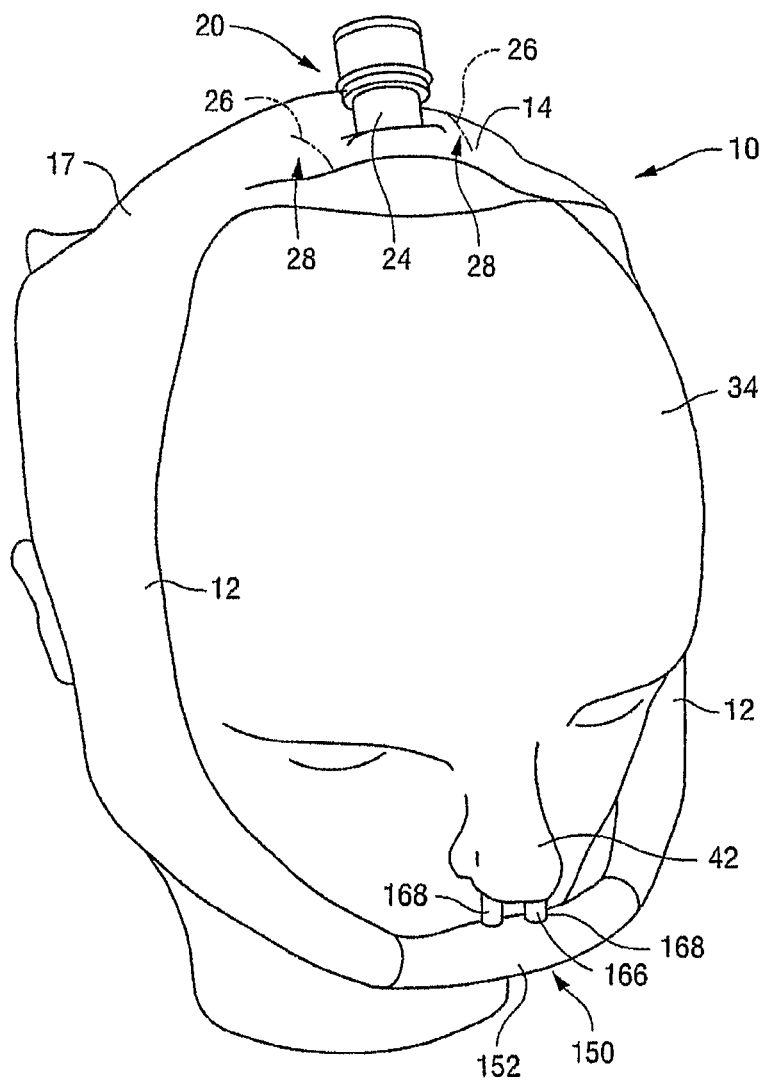
FIG. 3 is a perspective view of another embodiment of the headgear viewed from another angle to that shown in FIG. 1.

In FIGS. 1 and 3, the headgear 10 is shown mounted on a patient's head 34. As illustrated, the central portion 14 and T-connection 20 of the headgear 10 are configured to extend across the patient's head 34 at a position somewhat anterior of the apex 36 of the head 34, while the strap 16 is configured to extend around the portion of the head 34 posterior of the apex 36. The headgear 10 is designed to conform to the curvature of the occiput of the patient's head 34 so that the headgear 10 is stably seated thereon.

Also, as can be seen in FIGS. 1 and 3, the conduits 12 extend downwards on opposite sides of the patient's head 34 between the eye and ear 38 of the patient on each side of the head 34. The conduits 12 curve forwards towards their lower extremities, to terminate at second ends 40 (see FIG. 1) that are opposite to the first ends 28. The second ends 40 are adjacent to the patient's nose 42 and may be attached to a nasal interface or seal forming portion, such as the nose piece 150 referred to below (see FIG. 3) which is in contact with the patient's nose.

As shown in FIG. 1, attached to the second end 40 of each conduit 12 is a nose attachment formation or nasal/seal interface connector 44, having a part which extends via the respective second end 40, between the plastic sheets 17, to a position (not shown) within the conduit 12, and another portion 46 which is outside the conduit 12.

Each portion 46 of the nose attachment formation 44 is configured as a socket for receiving complementary formations which are connected to nose piece 150 as discussed below. The headgear may be provided with a pair of seal rings 46.1, each joined to the headgear at a respective aperture for establishing a close seal with the nose-piece 150.

In the illustrated embodiment, the sheets 17 are flocked (e.g., have a velvet-like texture) to provide comfort to the patient, and their attachment to each other is reinforced by stitching 52 (see FIG. 1). The headgear 10 may also be provided with a cover (not shown) of cloth or other material which will be comfortable to a patient, and the cover may have decorative effects, e.g., patterns or other markings, which may be attractive to a child patient.

A thin layer of foam rubber or other suitable padding (not shown) may be provided in selected locations between the inner surfaces of the sheets 17 to enhance the structural integrity of the headgear 10, or otherwise improve comfort to the patient especially on the bony regions of the face, e.g., the cheekbones.

Figure 4:
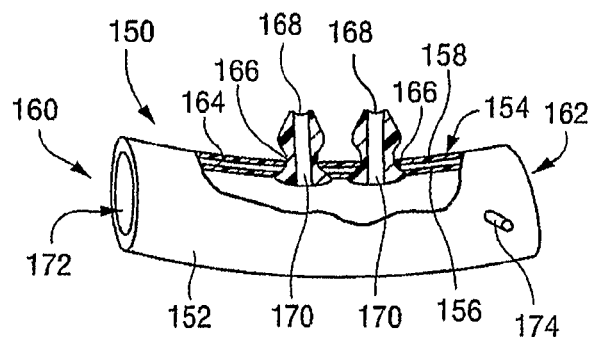
FIG. 4 is a perspective view, shown partly in cross-section, of a nose piece according to an embodiment of the invention.

Referring now to FIG. 4, the nose piece 150 is discussed in more detail. The nose piece 150 includes a conduit 152 having outer walls 154. The outer walls 154, in turn, are double walls, having inner wall portions 156 and outer wall portions 158. The inner wall portions 156 and outer wall portions 158 are sealingly joined to each other at first and second ends 160 and 162, respectively, of the nose piece 150. Each end 160 and 162 is configured for connection in fluid flow communication to the portion 46 of a respective nose attachment formation 44.

The inner wall portions 156 and outer wall portions 158 define, between them, an annular space 164 extending circumferentially with respect to the nose piece 150.

The conduit 152 defines a pair of apertures 166 each for accommodating a respective nostril formation 168 of flexible plastic or elastomer (e.g., silicone rubber) which extends through the relevant aperture 166. Each nostril formation 168 has a central passage 170. The nostril formations 168 are shaped to provide a close comfortable fit in the patient's nose 42, i.e., in the patient's nostrils. The nostril formations 168 may have any suitable form, e.g., nasal pillows, nasal prongs, cannula, or nasal puffs. If desired, the nostril formations 168 may be shaped and sized so as to be customized to a particular patient's nose.

The outer walls 154 of the nose piece 150 define a central passage 172 for establishing fluid flow communication between the interiors of the conduits 12 and passages 170 of the nostril formations 168, and hence with the patient's nose 42.

Similar to the headgear 10, the conduit 152 may be formed from sheets of polymeric (e.g., plastic) material which may be suitably joined by HF plastics welding to achieve the construction represented in FIG. 4.

Figure 9:
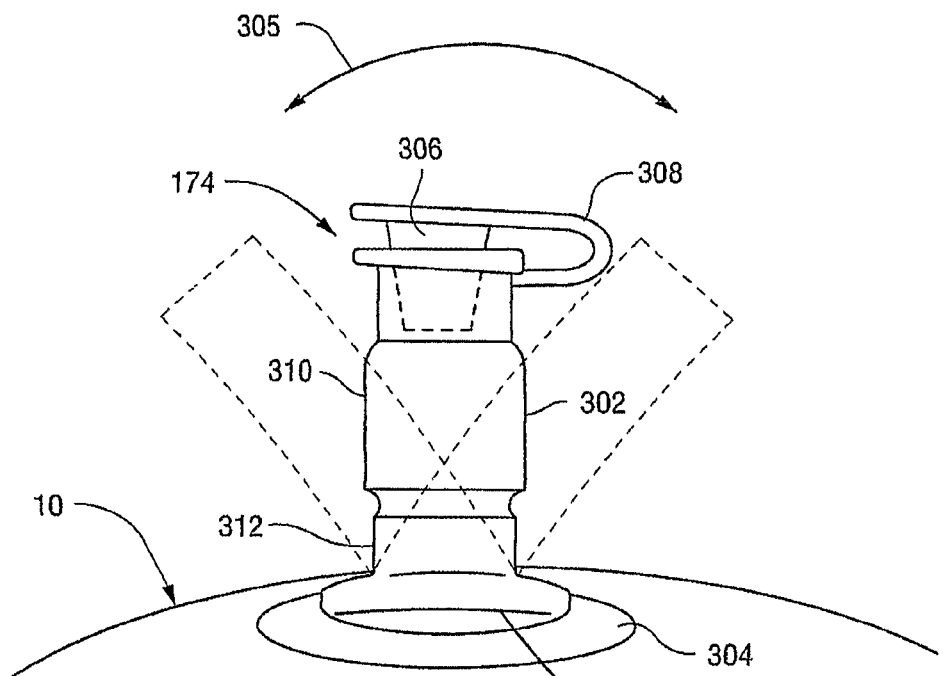
FIG. 9 is a one way inflation nipple.
Figure 9A:
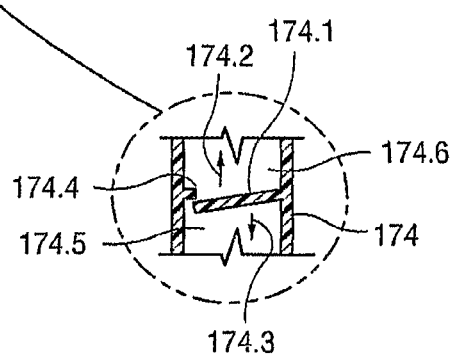
FIG. 9A is cross section through a portion of the nipple of FIG. 9.

Opening through the outer wall portion 158 of each nose piece 150, into the respective annular space 164, is an inflation nipple 175 having a one-way valve 174 which is illustrated in more detail in FIGS. 9 and 9A. The nipple 175 and one-way valve 174 permit the introduction of air into the annular space 164 so as to inflate the conduit 152 to provide it with sufficient rigidity to maintain its shape, while not depriving it of sufficient flexibility so as to be uncomfortable to the patient. The nipple 175 and valve 174 can thus be used to introduce more air into, or to remove air from, the annular space 164 so as to allow the rigidity or size of the conduit 152 to be adjusted to suit a particular patient or particular circumstances.

The nipple 175 may include a short tube 302. The nipple 175 includes a base 304 below the short tube 302, the base being joined, e.g., by plastics welding, to the nose piece 150 (or to the headgear 10 in the case of the headgear 10 being inflatable). The plastic material of the base 304 may be thinner than that of the remainder of the tube structure 300. This allows for twisting of the short tube 302 as represented in phantom lines, and by the arrow 305, in FIG. 9. The base 304 also is near the one way valve 174 as described below.

The nipple 175 also includes a cap 306 receivable as a tight but removable fit in the short tube 302 for closing off the short tube 302 and preventing the passage of air through it. As illustrated, a flexible cord 308 joins the cap 306 to an upper side position of the short tube 302. The flexibility of the cord 308 allows the cap 306 to be moved between its closure condition as shown in which it closes the short tube 302, and an open condition in which it is removed from the opening of the short tube 302.

The nipple 175 is also provided with an upper waist region 310 and a lower waist region 312 which is narrower that the upper waist region 310. These waist regions allow deformation of the nipple 175 by permitting the lower waist region 312 to be telescopically received within the upper waist region 310. This, in turn, allows the nipple 175 to be pressed into that portion of the nose piece 150 (or headgear 10 if the headgear 10 is inflatable) to which it is joined so that it becomes inverted within that portion, and effectively stowed away.

As described above, the base 304 of the nipple 175 is near the one way valve 174, which has a moveable flap 174.1. The moveable flap 174.1 extends from and is hinged to, and formed integrally with, the internal wall of short tube 302. The one way valve 174 includes a flange 174.4 which serves the purposes of a detent to prevent the flap 174.1 moving past the flange 174.4 in the direction of arrow 174.2, when the cavity 174.5 is under pressure. The flange 174.4 also provides a location for the edge of the flap 174.1 to seal against.

When the cavity 174.6 has a greater pressure therein than the cavity 174.5, e.g., when it is being inflated, the flap 174.1 will move in the direction of arrow 174.3 allowing inflation. As soon as there is a pressure differential, the flap 174.1 will move to a closed position, thereby acting as a one way valve. To deflate via the nipple 175, the user need only deform nipple 175 by compressing or squeezing the sides in the region of the one way valve 174, whereby the deformation will break the seal with the flange 174.4 allowing deflation.

In another embodiment, the nostril formations 168, instead of being separate formations of rigid plastic, may be integral with the conduit 152. In such an embodiment, the apertures 166 may be omitted.

In one form of this embodiment, the nostril formations 168 may have outer wall portions and inner wall portions which may be continuous with the outer wall portions 158 and inner wall portions 156, respectively, of the conduit 152, and which define between them a space which may be continuous with the annular space 164. Thus, inflation of the conduit 152 may also cause inflation of the nostril formations 168.

In a further embodiment as shown in FIG. 3, the nose piece 150 may be integral with the conduits 12 so that the headgear 10 and conduit 152 are of a unitary construction. In one form of this embodiment, the nostril formations 168 may be rigid plastics formations received in apertures 166 of the conduit 152. In another form of this embodiment, the nostril formations 168 may be integral and continuous with the conduit 152 as described above.

Figure 5:
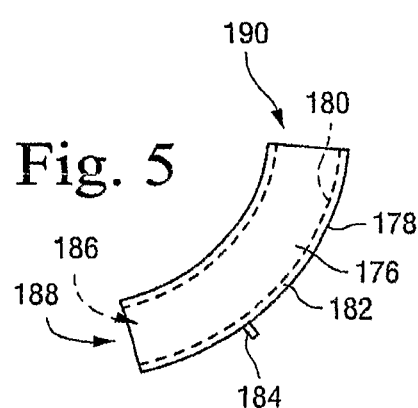
FIG. 5 is schematic plan view of a nose piece according to another embodiment of the invention.

In another embodiment as shown in FIG. 5, instead of having a nose piece which includes a conduit such as the conduit 152 and nostril formations such as the nostril formations 168, two inflatable curved nostril formations 176 (only one being shown) may be provided. In the illustrated embodiment, each nostril formation 176 has outer wall portions 178 and inner wall portions 180 defining a central enclosed annular space 182 between them, a one-way valve 184 for introducing air to the space 182 to inflate the nostril formation 176, and a central passage 186. In this embodiment, one end 188 of each nostril formation 176 is configured for attachment to the portion 46 of a respective nose attachment formation 44, while an opposite end 190 is configured for being received in the patient's nose 42. In an embodiment, the nostril formations 176 for each of the patient's two nostrils may be adapted to be attached to each other, to facilitate support of the nostril formations 176 and their sealing with the patient's nose.

In other embodiments, the nose pieces 150 or conduits 152 thereof may be other than the inflatable constructions as described above. They may, instead, have single outer walls of similar construction to the conduits 12.

For example, the nasal interface may be structured similar to nasal assemblies disclosed in U.S. patent Ser. No. 10/781, 929, which is incorporated herein by reference in its entirety.

Alternatively, the conduits 12, instead of having their walls formed of single plastic sheets as described above, may be made up of double walls having inner wall portions and outer wall portions similar to the inner wall portions 156 and outer wall portions 158, respectively, of the nose piece 150. These inner and outer wall portions would define a sealed and inflatable inner space similar to the space 164 of the nose pieces 150.

This construction of double walls may be used for the whole of the headgear 10, or selected portions of it. This would enable selected portions of the headgear 10, which are inflatable as a result of the double wall construction, to be inflatable as in the case of the conduits 152 of the nose piece 150, to achieve a desired amount of rigidity where required. The double wall construction would also serve to reduce noise transferred through the walls.

In one embodiment, an inner skeleton may be provided in some or all parts of the above equipment where such double walls are provided in the cavity between the relevant inner and outer wall portions. The inner skeleton may be comprised, for example, of spring wire, and this could be configured in an expanded condition to provide further structural support where the skeleton is used.

In use, as described in relation to FIG. 1, the headgear 10 is placed on the head 34 of the patient. The T-connection 20 is connected to a supply pipe (not shown) of an air supply (also not shown) configured for supplying air under a positive pressure. The supply pipe will include an end for attachment to the attachment formation 30 for effecting a seal with the T-connection 20.

In another embodiment or in combination with the embodiment described above, a suitable structure may be provided for minimizing the extent to which the supply pipe pulls on the headgear 10. This structure may involve a pivotable pipe connection, a ball-and-socket connection, or a flexible bellows connection (such as that described in the next paragraph) to the T-connection 20, or to another part 290 (FIG. 12) of the relevant headgear in an embodiment where there is no such T-connection. This may facilitate stability of the headgear 10 by reducing the extent to which drag forces on the supply pipe are transferred to the headgear 10.

Figure 10:
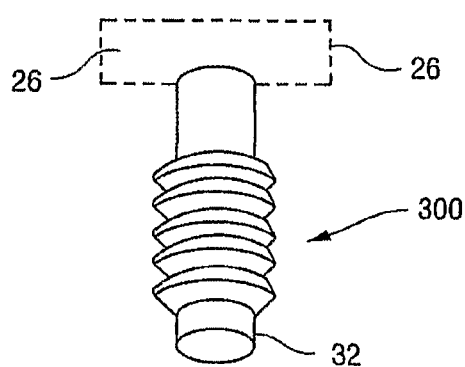
FIG. 10 is a perspective view of a tube structure for connecting a headgear to an air supply pipe.

The attachment formation 30 may include a concertina tube 300 as illustrated in FIG. 10, which terminates in a cylindrical union 32. The tube 300 may allow for relative rotation of the air supply coupling thereby preventing the transfer of bending forces which would otherwise uncouple the air supply connection.

The supplied air passes into the central pipe 24 of the T-connection 20 and then via the side pipes 22 into the conduits 12. As the air is under a positive pressure, it serves to inflate the conduits 12 so that they define central passages extending from their respective first ends 28 to their respective second ends 40. The air then passes via the nose attachment formations 44 and nose piece 150, into the patient's nose 42 (i.e., the nostrils).

The headgear 10 may be custom fit to a particular patient's head 34. This may be achieved by scanning or mapping the head 34 to determine its shape in a three-dimensional sense, and then cutting the sheets 17 so that when the sheets 17 are joined to each other they form a headgear 10 which is suitable for achieving a close and comfortable fit on the patient's head 34. It will be appreciated that there may be as many different shapes of the headgear 10 as there are patient's heads 34. In addition, once a particular shape is determined in which to form a sheet 17 in relation to a particular patient's head, or in relation to a particular type of head shape (which may apply to more than one patient), there is no limitation on the number of sheets that may be cut to a particular sheet shape to form a particular headgear.

Figure 7:
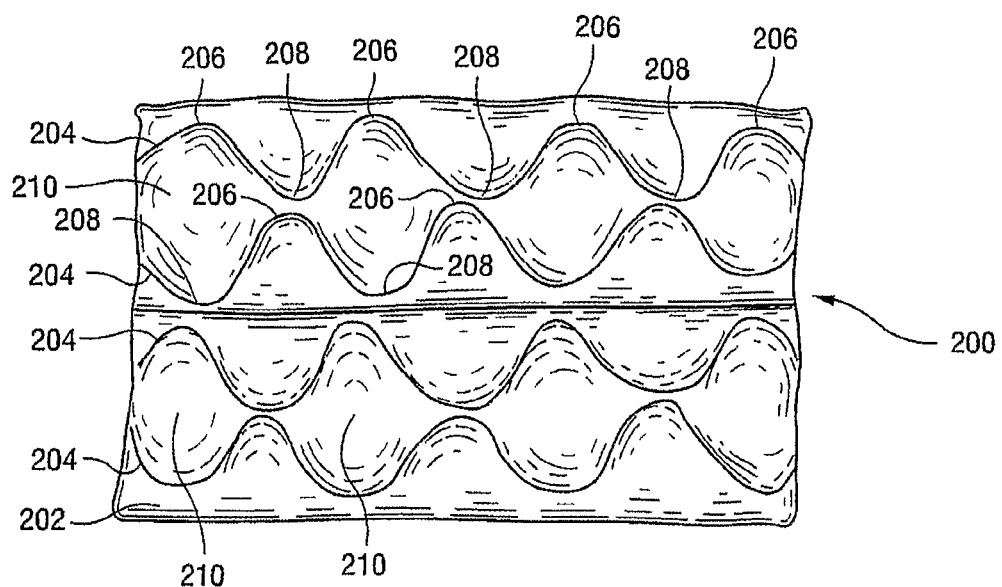
FIG. 7 is a schematic perspective view of a cushion indicative of a manner of forming a headgear according to an embodiment of the invention.
Figure 8:
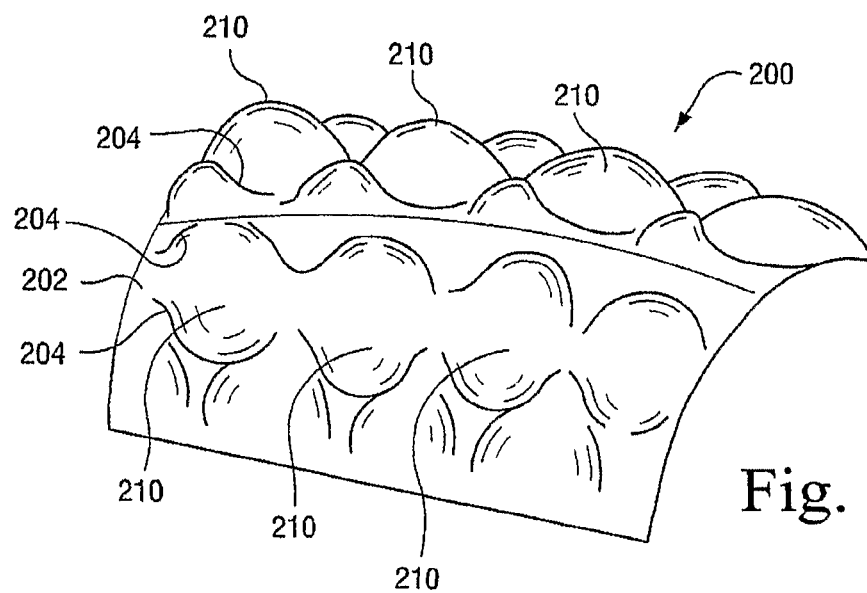
FIG. 8 is a schematic elevation of the cushion of FIG. 7 in a formed condition.

In an embodiment, the sheets 17 may be joined along predetermined joint paths. In this regard, reference is made to the cushion 200 shown in FIGS. 7 and 8, which has two sheets 202 (only one being shown) joined along paths 204. It will be seen that the paths 204 are of a sinusoidal, zig-zag shape with peaks 206 and troughs 208 such as may be found in quilting-like formations. The troughs 208 of each path 204 are aligned with the peaks 206 of the next path and vice versa, so as to form substantially diamond-shaped areas 210 between the paths where the sheets 202 are not connected to each other. In an embodiment of the headgear 10 under discussion, the headgear 10 may be formed with the sheets 17 being joined to each other in a similar fashion to the sheets 202, with the paths serving as fold lines to facilitate curving of the joined sheets 17 (as represented by the curving of the cushion 200 in FIG. 8) to conform to the shape of the head 34.

The regions of the headgear 10 corresponding to the diamond-shaped areas 210 of the cushion 200 may be inflated to form a number of juxtaposed cushioned zones to provide added comfort to the patient and to facilitate the firm and even seating of the headgear 10 on the patient's head 34.

Alternatively, instead of using the mapping to determine the shape in which the sheets 17 are to be cut as described above, the mapping may be used to form part of a headgear by forming a thermoplastic polymer in the shape of the patient's head 34.

The shaping of the headgear 10 to suit the particular shape of a patient's head 34 may significantly assist in achieving a headgear 10 having conduits 12, a central portion 14, and a strap 16 which are snugly fitted to the patient's head 34. This may achieve an effective distribution of pressure between the headgear 10 and the patient's head 34 rather than having specific locations at which there are high pressure points and other locations at which there is insufficient pressure. This, in turn, facilitates the secure attachment of the headgear 10 to the patient's head 34.

In addition, the unitary construction of the conduit 12, central portion 14 and strap 16, with the headgear 10 being specifically suited to a particular patient's head 34, eliminates the need for adjustment parts of the headgear 10 which would otherwise be required to fasten the headgear 10 securely to the patient's head 34. This unitary construction also simplifies the donning of the headgear 10 and removal thereof from the patient's head.

The snug securing of the headgear 10 to the patient's head 34 may be further facilitated in those embodiments of the headgear 10 having double walls, or portions with double walls as referred to above. In these embodiments, inflation of the double walls (i.e., provision of inflating air into the space between the double walls) causes the respective inner wall portions to press more firmly against the patient's head 34. This can be particularly useful in relation to those parts of the patient's head 34 which are of a substantially concave or recessed shape, such as immediately in front of the patient's ears 38.

With the nose piece 150 being joined to the conduits 12 as described above, the air supplied into the center pipe 24 of the T-connection 20, after having passed through the passages of the conduits 12, proceeds to pass along the passage 166 of the conduit 152 of the nose piece 150, and into the patient's nose 42.

Exhalation by the patient is facilitated by using a material for the plastic sheets 17 which is to some extent gas permeable, preferably in the vicinity of the nose 42 of the patient. This will allow for a certain amount of leakage or venting of air and exhaled carbon dioxide therethrough. A suitable thermoplastic elastomer, e.g., a poly-olefin, may be used for this purpose. Alternatively, the sheets 17, instead of being fully of plastic, may be wholly, or may have parts, made of other types of gas permeable material, e.g., silk or other woven material, or the Polytetrafluoroethylene (PTFE) material known as GORETEX®.

As the patient breathes out, the exhaled breath can then pass via the nose pieces 150 and then through the walls of the conduits 12 at positions close to the respective second ends 40 thereof.

A particularly suitable material for the sheets may be breathable polyurethane which allows the passage of water vapour with the escaping air, but provides a substantially airtight passage. By the expression "substantially airtight," it is meant that sufficient resistance to the passage of air therethrough is provided to prevent too much air from escaping. The ability to allow water vapour to pass through is advantageous as it may assist in avoiding an undesirable accumulation of moisture originating from gases exhaled by the patient, in the interior passages of the conduits 12. Materials that may provide these properties include those manufactured by the Darlington Corporation known by the trademark DARLEXX®, or the 3M product known by the trademark THINSULATE®, or the Polytetrafluoroethylene (PTFE) material known as GORETEX®, or the product known as ATLANTECH' made by Atlantis Weather Gear Inc.

With the walls of the conduits 12, or parts thereof, being gas permeable as described above, some of the air supplied via the center pipe 24 of the T-connection 20 will also escape from the conduits 12. This arrangement and the flexible nature of the passageways can assist in a reduction in the noise generated by the passage of air via the conduit 12 to the nose pieces 150.

The passage of exhaled gas through the walls of the conduits 12 may also provide a useful means for allowing heat to escape from the headgear 10. Such heat, if not allowed to escape in this manner, may result in the headgear 10 becoming so heated as to be unnecessarily uncomfortable for the patient. In addition, the gas permeability of the materials used, as referred to above, may permit the passage of heat and water vapour through the parts of the headgear on top of the patient's head 34 to improve comfort, especially in warmer weather. The construction of the headgear 10, and particularly its unitary nature, has the advantage that, if the headgear 10 is being worn by the patient, and the patient rolls his or her head 34 onto a surface such as a pillow so that one of the conduits 12 is flattened by the pressure of the patient's head 34 on the pillow, all or most of the air that would have passed through that conduit 12 but which is prevented from doing so due to the constriction of the conduit's passage is permitted to pass instead through the other conduit 12. This is enabled due to the flexibility of the conduits 12 and their resultant ability to expand and substantially collapse. Thus, the total volume flow rate of the air through the pair of conduits remains substantially constant during the flattening and expansion of the respective conduits. Depending on the configuration and cross-sectional shapes of the conduits 12 when the above flattening and expansion occurs, the collapsing of the conduit 12 causes a change in the ratio between a height extent and a lateral extent of that conduit, with the height extent decreasing and the lateral extent increasing. Similarly, the deformation of the other conduit causes a change in the ratio between its height extent and lateral extent with the height extent increasing and the lateral extent decreasing.

In an embodiment, the headgear may include an adjustable head cap with the conduits being attached to the cap at opposite sides thereof. In this case, the cap may constitute the attachment means, and the connection means may be mounted on the cap.

In another embodiment, the conduits may be detachable from the attachment means so that the attachment means may be selectively releasably connected with differently sized and/or shaped conduits. In this case, the conduits may be selectively releasably connected with differently sized and/or shaped attachment means, whereby the headgear may form part of a modular headgear system having interchangeable attachment means and conduits.

In yet another embodiment, the headgear may be adapted for use with a patient mask, the mask being configured to fit the patient's head adjacent the patient's nose to direct gas from the conduits to the nose. Then, the headgear may be adapted to be detachable from the mask to enable the patient to selectively remove the mask from the headgear and hence from the patient's head while the headgear continues to be being worn by the patient.

A particular advantage of the headgear 10 as described is that, when not in use, the T-connection 20 may be removed from the aperture 18. Then, the conduit 12, the central portion 14, and the strap 16 may be flattened out so as to collapse the passages of the conduits 12, and rolled up or folded for storage purposes, so that a minimum of storage room is required. On the other hand, when in use, the passage of air itself through the conduits 12 serves to inflate the passages and to press the inside walls of the conduits 12 firmly against the sides of the patient's head 34 to achieve a comfortable and snug fit.

The headgear 10 has various advantages. For example, an advantage of the headgear 10 is that the T-connection 20 is located in use at a position of the patient's head which is unlikely to be subjected to any compression force due, for example, to the patient's head being on a pillow. Thus, while the conduits 12 are flexible and should therefore not provide much discomfort to the patient even if the patient lies on them, this should not be an issue in respect of the relatively hard T-connection 20, due to the location of this component.

In addition, the relative flexibility and hence softness of the material from which the conduits 12, the central portion 14 and strap 16 are formed allows the headgear 10 to be engaged with parts of the patient's head, such as the patient's cheeks, that may have been too sensitive for engagement with prior art devices.

The fact that the conduits 12 and central portion 14 define most of the passageways through which air needs to travel to be delivered to the patient means that the need for additional tubing and tubing securement straps may be avoided. Therefore, this also avoids the bulk and weight that such additional tubing and securement straps might involve.

The ability of one of the conduits 12 to expand to allow for a greater volume flow rate when the other conduit 12 is compressed or collapsed so as to be generally flat against the patient's face (e.g., when the patient lies on the other conduit 12 on a pillow) enhances the patient's comfort and minimizes discomfort that might have been caused if more inflexible tubing were used. It also reduces discomfort that may be caused by engagement of the headgear 10 with contact pressure points on the patient's head 34.

The use of plastics welding as described above for manufacturing the headgear 10 avoids the need for clips, buckles, adjustment straps and the like, thus providing for greater simplicity of use. In addition, the forming of the headgear 10 to suit the shape of the patient's head 34 and the inherent lightweight nature of the headgear 10 assists in providing greater comfort to the patient.

Figure 6:
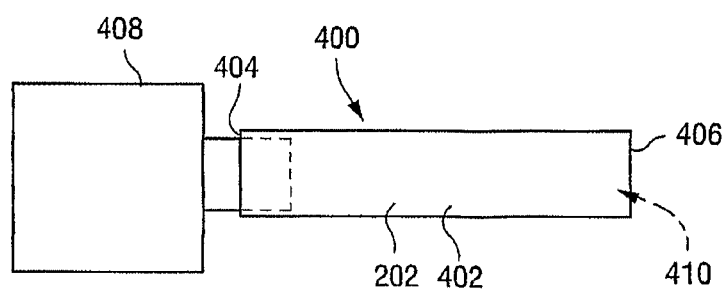
FIG. 6 is a schematic elevation of a conduit according to an embodiment of the invention, the conduit shown attached to an air supply.

Referring to FIG. 6, there is shown a schematic representation of a PAP machine conduit 400 according to an embodiment of the invention. The conduit 400 has flexible conduit walls 402, and has a first end 404 and a second end 406. The first end 404 is attached to a supply means 408 for supplying air under a positive pressure. As in the case of the conduits 12 described above, the conduit 400 is collapsible. As air under a positive pressure is supplied by the supply means 408, the pressure of the air urges the walls 402 into the condition shown, in which the walls 402 define a central passage 410 of the conduit 400. Thus, the air may pass along the passage 410 to the second end 406, where the air may be directed as required.

As an alternative to the walls 402 being urged into the condition shown only by the pressure of the air, a collapsible spring may be provided which assists in preventing kinking of the conduit 400 in use.

The flexibility of the walls 402 allows the conduit 400 to be folded or rolled to a compact size during storage or travel. In addition, these walls may be of a single wall type or a double wall type similar to the walls 154 described above. Such a double wall construction may also provide enhanced insulation to assist in regulating the temperature of the air from the air supply means 408.

Figure 11:
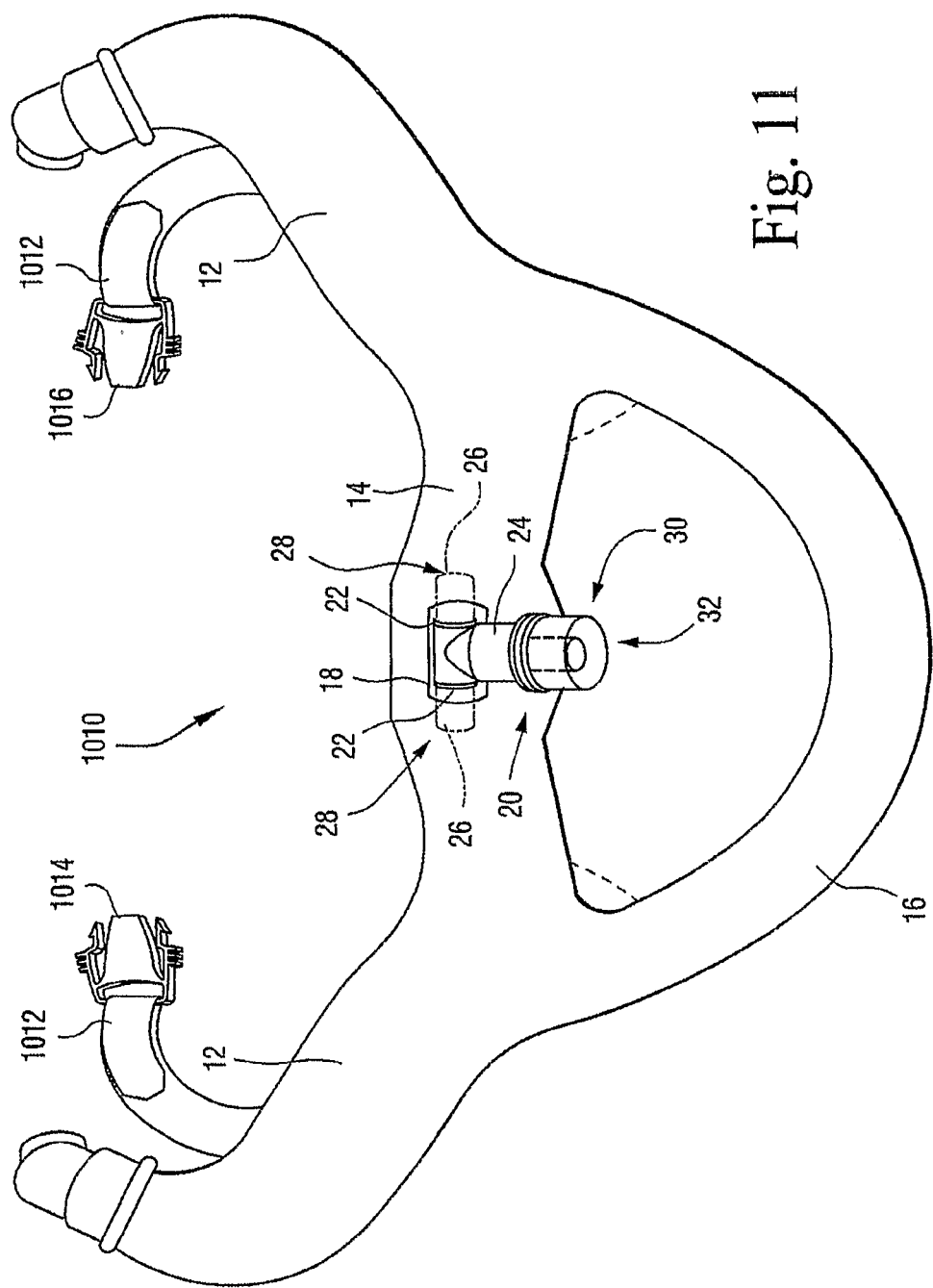
FIG. 11 is a plan view of headgear similar to that of FIGS. 1 and 2, showing a strap system included with the headgear.

Illustrated in FIG. 11 is headgear 1010, which is similar to the headgear 10 of FIGS. 1 and 2, and accordingly, like parts have been like numbered. The headgear 1010 differs from the headgear 10 in that two straps 1012 are provided, each of which is connected to and extends from a respective one of the conduits or side portions 12 of the headgear 10.

The straps 1012 respectively terminate in buckle members 1014 and 1016 which can connect to a mask or nose piece and allow a user to secure the headgear 1010 to his or her head. The straps 1012 may provide for adjustability of the strap length.

Figure 12:
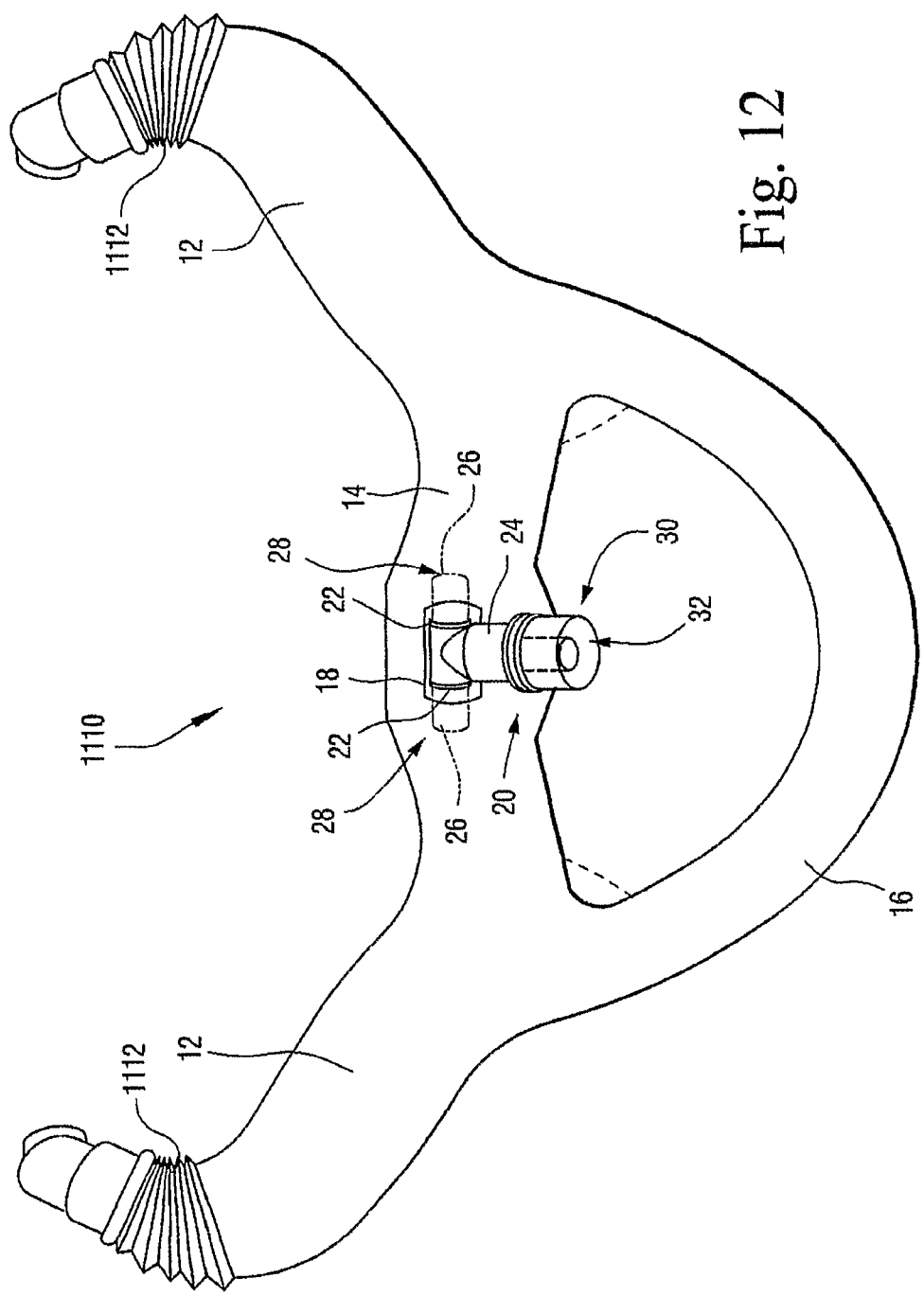
FIG. 12 is a plan view of headgear similar to that of FIGS. 1 and 2, showing a collapsible cuff included on the ends of the conduits of the headgear.

Illustrated in FIG. 12 is headgear 1110, which is similar to the headgear 10 of FIGS. 1 and 2, and accordingly, like parts have been like numbered. The headgear 1110 differs from the headgear 10 in that a collapsible cuff 1112 is provided on ends of each of the conduits or side portions 12. As illustrated, the collapsible cuff 1112 is of a bellows formation. The collapsible cuff 1112 allows the length of the ends of the conduits 12 to be adjusted by extension or contraction, as required.

It will be understood that the invention disclosed and defined herein extends to all alternative combinations of two or more of the individual features mentioned or evident from the text. All of these different combinations constitute various alternative aspects of the invention.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike.

What is claimed is:

1. A patient interface assembly for delivering a supply of pressurized gas to a patient for treatment of sleep disordered breathing, the patient interface assembly comprising:
   a patient interface configured to engage the patient's face to direct the supply of pressurized gas to an airway of the patient for treatment of sleep disordered breathing; and
   headgear to support the patient interface in a desired position on the patient's face, the headgear including:
      a pair of flexible conduits configured to support the patient interface and to deliver the supply of gas to the patient interface in use, each conduit having a top portion in fluid communication with the supply of gas and a bottom portion adapted to, in use, be connected to the patient interface, each conduit being arranged to, in use, extend along a respective side of the patient's head between the patient's eye and ear; and
      a strap extending between the pair of conduits and adapted to engage a rear portion of the patient's head when the patient interface assembly is worn, wherein the patient interface assembly does not include additional conduit tubing and does not include an additional securement strap, and
      wherein each conduit includes a foam inner layer and a fabric outer layer provided over the foam inner layer such that the fabric outer layer provides an outer surface of the conduit configured to contact the patient's skin in use.

2. The patient interface assembly according to claim 1, wherein each conduit comprises a lamination of a plurality of materials.

3. The patient interface assembly according to claim 2, wherein the foam inner layer and the fabric outer layer are laminated.

4. The patient interface assembly according to claim 3, wherein a portion of the pair of flexible conduits includes a gas permeable material to allow exhaust gases to pass therethrough to atmosphere.

5. The patient interface assembly according to claim 1, wherein the conduits comprise an elastomer.

6. The patient interface assembly according to claim 1, further comprising an air connector configured to be fluidly connected to the supply of pressurized gas, the air connector being adapted to be stably positioned at the top of the patient's head when the patient interface assembly is worn.

7. The patient interface assembly according to claim 6, said headgear further comprising a central portion disposed between the pair of conduits to fluidly join the top portions of the conduits, the central portion being configured to contact the top of the patient's head when the patient interface assembly is worn.

8. The patient interface assembly according to claim 7, wherein the air connector is directly attached to the central portion.

9. The patient interface assembly according to claim 8, wherein the air connector is relatively rigid as compared to the pair of conduits and the central portion.

10. The patient interface assembly according to claim 9, said central portion further comprising an aperture formed therein, a first portion of the air connector extending into the aperture and within the central portion while a second portion of the air connector protrudes away from the aperture and extends exterior to the central portion.

11. The patient interface assembly according to claim 8, wherein the air connector enables movement of an air supply tube with respect to the central portion to reduce tube drag.

12. The patient interface assembly according to claim 11, wherein the air connector comprises a swivel coupling device.

13. The patient interface assembly according to claim 12, wherein the swivel coupling device has a coaxial arrangement with the air connector.

14. The patient interface assembly according to claim 8, wherein the central portion is arranged such that the air connector is adapted to be positioned anterior of an apex of the patient's head when the patient interface assembly is worn.

15. The patient interface assembly according to claim 1, wherein the pair of conduits is shaped to match a contour of the patient's head.

16. The patient interface assembly according to claim 1, wherein each conduit comprises a conduit wall that is deformable between (a) an open condition in which the conduit wall defines a conduit passage along which the pressurized gas can travel from the top portion to the bottom portion, and (b) a collapsed condition in which the conduit wall substantially collapses the conduit passage.

17. The patient interface assembly according to claim 16, wherein each conduit is configured to deform into the collapsed condition under the weight of the patient's head.

18. The patient interface assembly according to claim 1, wherein the strap is respectively connected to the pair of conduits at a first attachment point and a second attachment point that are arranged to be positioned superior to the patient's ear when the patient interface assembly is worn.

19. The patient interface assembly according to claim 18, wherein the strap is integrally formed with the pair of conduits.

20. The patient interface assembly of claim 1, further comprising an interface connector attached to the bottom portion of each conduit, each interface connector being removably connected to a respective side of the patient interface.

21. The patient interface assembly of claim 20, wherein each interface connector includes a connection portion that extends from the respective conduit to connect with the patient interface.

22. The patient interface assembly of claim 20, wherein the patient interface includes two complimentary formations on opposing sides thereof to mate with a respective one of the interface connectors.

23. The patient interface assembly of claim 1, further comprising a vent in the vicinity of the patient's nose to allow exhaled carbon dioxide to pass to atmosphere.

24. The patient interface assembly of claim 1, wherein the patient interface is a nasal interface configured to engage the patient's nose in use.

25. The patient interface assembly of claim 1, wherein the foam inner layer and the fabric outer layer are laminated, and the fabric outer layer is configured to contact the patient's skin in use,
   further comprising an air connector configured to be fluidly connected to the supply of pressurized gas, the air connector being adapted to be positioned on top of the patient's head when the patient interface assembly is worn,
   said headgear further comprising a central portion disposed between the pair of conduits to fluidly join the top portions of the conduits, the central portion being configured to contact the top of the patient's head when the patient interface assembly is worn,
   wherein the air connector is directly attached to the central portion, an aperture being formed in the central portion and the air connector extending into the aperture,
   wherein the air connector is relatively rigid as compared to the pair of conduits and the central portion,
   wherein the air connector enables movement of an air supply tube with respect to the central portion to reduce tube drag,
   wherein the air connector comprises a swivel coupling device, the swivel coupling device having a coaxial arrangement with the air connector,
   wherein the central portion is arranged such that the air connector is adapted to be positioned anterior of an apex of the patient's head when the patient interface assembly is worn,
   wherein each conduit comprises a conduit wall that is deformable between (a) an open condition in which the conduit wall defines a conduit passage along which the pressurized gas can travel from the top portion to the bottom portion, and (b) a collapsed condition in which the conduit wall substantially collapses the conduit passage,
   wherein each conduit is configured to deform into the collapsed condition under the weight of the patient's head,
   further comprising an interface connector attached to the bottom portion of each conduit, each interface connector being removably connected to a respective side of the patient interface, each interface connector including a connection portion that extends from the respective conduit to connect with the patient interface, and
   wherein the patient interface includes two complimentary formations on opposing sides thereof to mate with a respective one of the interface connectors.

26. The patient interface assembly of claim 1, wherein each conduit includes a portion configured to extend along a respective side of the patient's head in use, each portion including 1) a first section having a width that gradually decreases along a length of the conduit in a direction towards the bottom portion, and 2) a second section relatively proximate the bottom portion as compared to the first section, the second section having a width that gradually increases along a length of the conduit in the direction towards the bottom portion.

27. The patient interface assembly of claim 26, wherein the first section is directly adjacent the second section such that no other sections of the conduit are disposed between the first section and the second section.

28. The patient interface assembly of claim 27, wherein both the first section and the second section of each conduit are inferior to the strap when the patient interface assembly is worn.

29. The patient interface assembly of claim 27, wherein the strap is respectively connected to the pair of conduits at a first attachment point and a second attachment point, and
   wherein both the first section and the second section of each conduit are inferior to the first attachment point and a second attachment point when the patient interface assembly is worn.

30. The patient interface assembly of claim 29, wherein each conduit includes a third section that is superior to the first attachment point and the second attachment point when the patient interface assembly is worn,
   wherein the third section of each conduit is wider than at least the first section.

31. The patient interface assembly of claim 7, wherein the air connector is removably attached to the central portion.

32. The patient interface assembly of claim 10, wherein the conduits, the central portion and the interface form a ring with a ring-shaped gas passageway,
   said aperture in the central portion being adapted to be in fluid communication with an air supply tube, and
   wherein the first portion of the air connector is firmly engaged with at least a portion of the central portion that is disposed along the ring.

33. The patient interface assembly of claim 10, wherein the conduits, the central portion and the interface form a ring with a ring-shaped gas passageway,
   said aperture in the central portion being adapted to be in fluid communication with an air supply tube, and
   wherein the first portion of the air connector extends into the ring formed by the conduits, the central portion and the interface.

34. The patient interface assembly of claim 33, wherein the central portion has a bottom wall configured to directly contact the patient's head and a top wall opposite the bottom wall when the patient interface assembly is worn, the top wall of the central portion having the aperture formed therein, and
   wherein the bottom wall of the central portion and the top wall of the central portion are spaced apart so as to form a portion of the ring-shaped gas passageway therebetween.

35. The patient interface assembly of claim 34, wherein the bottom wall of the central portion is configured to conform to a shape of the patient's head when the patient interface assembly is worn.

36. The patient interface assembly of claim 33, wherein the second portion of the air connector is configured to connect to the air supply tube, the second portion of the air connector being movable relative to the first portion of the air connector to enable movement of the air supply tube with respect to the central portion to reduce tube drag.

37. The patient interface assembly according to claim 36, wherein the air connector comprises a pivotable pipe structure, a ball-and-socket structure or a bellows structure to enable the second portion of the air connector to be movable relative to the first portion of the air connector.

38. The patient interface assembly according to claim 10, wherein the first portion of the air connector has an end portion disposed within an interior of the central portion, an exterior surface of the end portion extending laterally within the central portion in a direction of each of the conduits.

39. The patient interface assembly according to claim 1, wherein the bottom portion of each conduit is connected the patient interface via an interface connector.

40. The patient interface assembly according to claim 1, wherein each conduit is configured to inflate, upon introduction of pressurized air, into an open condition forming a conduit passage.

41. The patient interface assembly according to claim 1, wherein each conduit comprises a conduit wall that is deformable between (a) the open condition in which the conduit wall defines the conduit passage along which the pressurized gas can travel from the top portion to the bottom portion, and (b) a collapsed condition in which the conduit wall substantially collapses the conduit passage.

42. The patient interface assembly according to claim 41, wherein each conduit is configured to deform into the collapsed condition under the weight of the patient's head.

43. The patient interface assembly of claim 42, wherein each conduit is configured to accommodate an increase in volume flow rate of pressurized gas through the conduit when the conduit passage of the other conduit is in the collapsed condition.

44. The patient interface assembly of claim 41, wherein the conduits are configured such that a total volume flow rate of pressurized gas through the conduits remains substantially constant even if one of the conduits is deformed into the collapsed condition.

* * * * *